United States Patent [19]

Klatt et al.

[11] 4,063,548
[45] Dec. 20, 1977

[54] METHOD AND APPARATUS FOR MICTURITION ANALYSIS

[75] Inventors: William M. Klatt, Robbinsdale; Wayne H. Graves, Minnetonka; Robert E. Buuck, Golden Valley, all of Minn.

[73] Assignee: American Medical Systems, Inc., Golden Valley, Minn.

[21] Appl. No.: 566,044

[22] Filed: Apr. 7, 1975

[51] Int. Cl.² ............................................. A61B 5/10
[52] U.S. Cl. ................................. 128/2 R; 128/2 S; 128/2.1 E; 128/2.1 M; 128/349 R
[58] Field of Search ......... 128/2 R, 2 S, 2 N, 2.05 D, 128/20.5 E, 2.1 M, 2.1 R, 2.1 E, 344, 348 R, 349 R, 349 B, 2.06 E, 2.06 G, DIG. 4, DIG. 13, 404, 418, 419 P, 172.1, 184

[56] References Cited

U.S. PATENT DOCUMENTS

| | | | |
|---|---|---|---|
| 3,280,270 | 10/1966 | Allington | 128/2.06 G |
| 3,428,046 | 2/1969 | Remer et al. | 128/349 R |
| 3,437,088 | 4/1969 | Bielinski | 128/2 R |
| 3,568,660 | 3/1971 | Crites | 128/2.1 F |
| 3,628,538 | 12/1971 | Vincent et al. | 128/2.1 M |
| 3,641,993 | 2/1972 | Gaarder | 128/2.1 M |
| 3,674,010 | 7/1972 | Falenks | 128/2 R |
| 3,680,544 | 8/1972 | Shinnick et al. | 128/172.1 |
| 3,774,593 | 11/1973 | Hakata et al. | 128/2.1 M |
| 3,815,611 | 6/1974 | Denniston | 128/2 S |
| 3,870,072 | 3/1975 | Lindemann | 128/2 R |
| 3,897,682 | 8/1975 | Brooks | 128/2 S |

OTHER PUBLICATIONS

Bradley, et al., "Cystometric and Sphincter . . . Sclerosis," Neurology, vol. 23, No. 10, Oct. 1973, pp. 1131–1139.
Bradley, et al., "Neuro–Urological Selection . . . Micturition Reflex," *Neural Organization and Its Relevance to Prosthetics*, Intercontinental Med. Book Corp., New York, 1973, pp. 295–310.
Bradley, et al., "Sphincter Electromyography," Urologic Clinics of North America, vol. 1, No. 1, Feb. 1974, pp. 69–80.
Chatterjee, et al., "Multipurpose Flotation Catheter . . . Montonns," The Am. J. of Cardiology, vol. 33, Jan. 1974, p. 130.

*Primary Examiner*—Stephen C. Pellegrino
*Assistant Examiner*—Lee S. Cohen
*Attorney, Agent, or Firm*—Williamson, Bains, Moore & Hansen

[57] ABSTRACT

A method and apparatus for analyzing micturition disturbances are provided. The apparatus comprises a gas cystometry system for monitoring bladder detrusor reflexes and an electromyographic monitoring system which, in the preferred form of this invention, are combined within a unitary enclosure. The cystometry system further compromises a catheter for injecting fluid interiorly of the bladder and associated electronic circuitry for deriving interior bladder pressure. The electromyographic system comprises one or more electrodes for sensing sphincter electrical activity and electronic circuitry interconnected with the electrodes for amplifying sphincter electrical outputs. A dual trace strip chart recorder interconnected with the cystometry apparatus and the electromyography apparatus provides simultaneous display of bladder detrusor reflexes and related sphincter electrical activity for correlated analysis by the attendant physician. In the preferred embodiment of this invention the electromyographic electrodes are operably mounted at the bladder-engaging end of a cystometric catheter.

A method disclosed herein for diagnosing micturition dysfunction comprises the steps of generating a cystometrogram, generating a sphincter electromyogram, and simultaneously displaying the cystometrogram and the electromyogram to thereby correlate micturition neurological responses.

17 Claims, 10 Drawing Figures

U.S. Patent  Dec. 20, 1977  Sheet 1 of 4  4,063,548
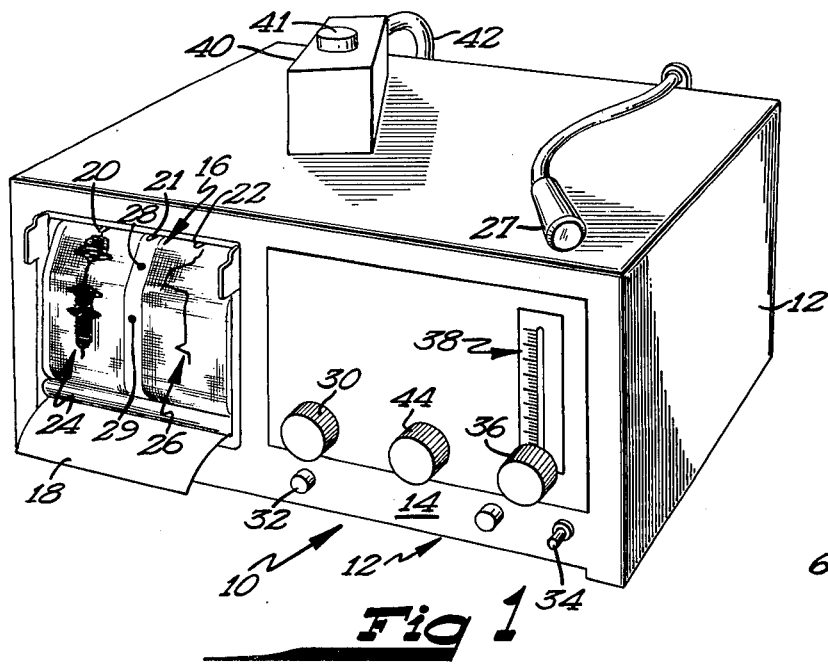

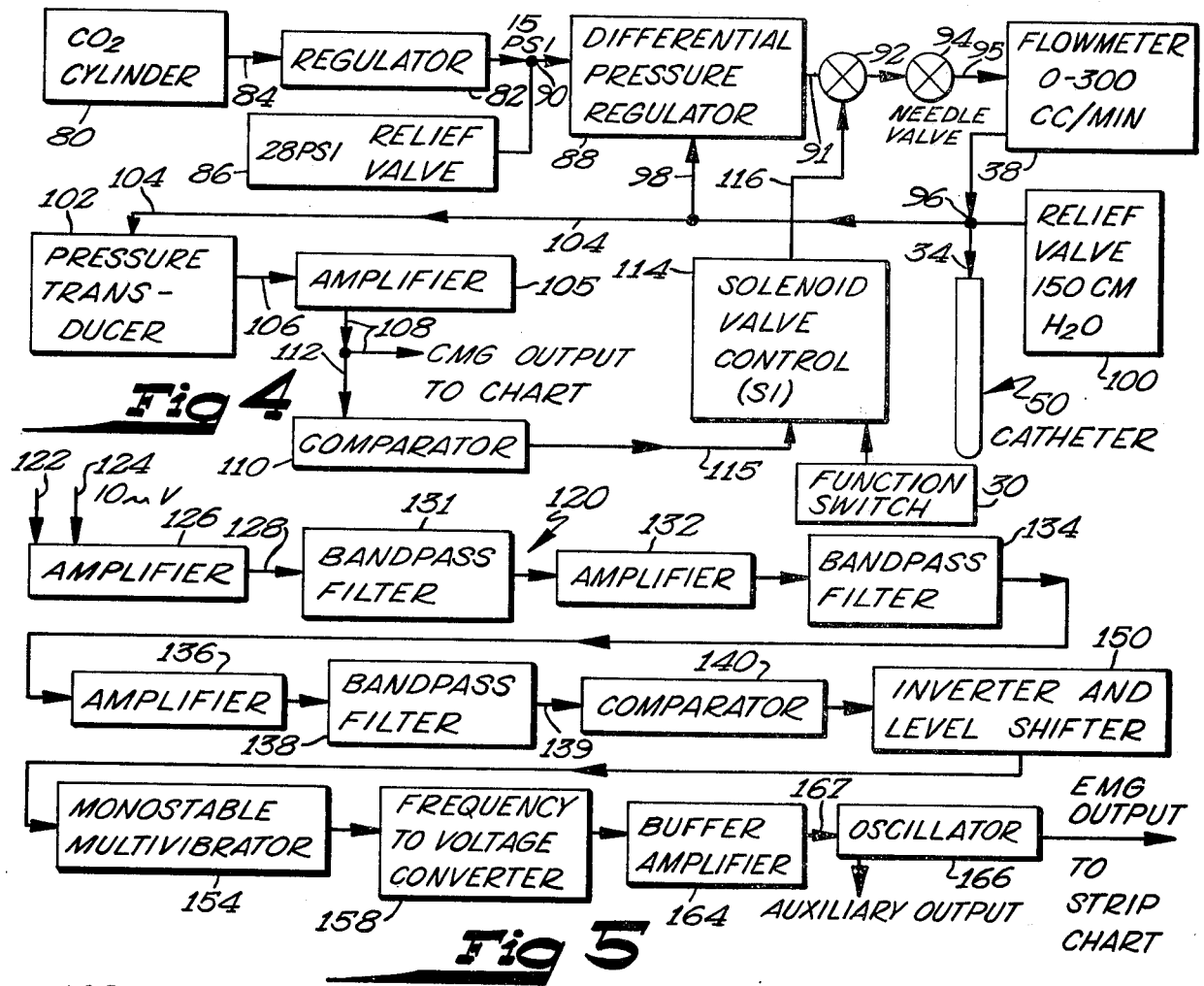
Fig 4
Fig 5
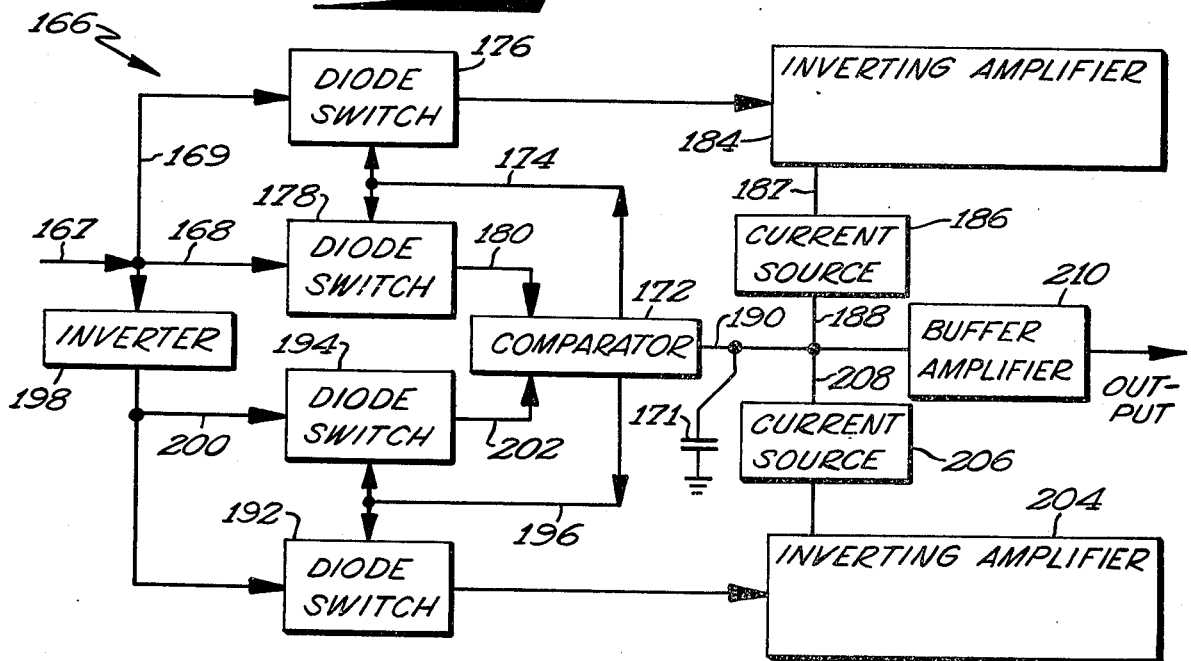
Fig 7

METHOD AND APPARATUS FOR MICTURITION ANALYSIS

BACKGROUND OF THE INVENTION

The micturition reflex is comprised of a plurality of interrelated neurological reflexes involved in urination. The function of the lower urinary tract includes maintenance of urinary continence and periodic expulsion of urine during voiding. The latter functions involve sympathetic, parasympathetic and somatic nerves. Continence is maintainable by sphincter muscles, which preferably controllably contract the bladder urethra, acting as a valve. Discharge of urine is facilitated by sphincter relaxation. Urination also requires coordinated operation of the detrusor muscle which surrounds the bladder. Impairment of one or more of the neurological reflexes associated with proper sphincter or detrusor action can result in inefficient or impaired bladder operation. Damage can occur to the urinary tract as a result of injury or diseases, such as multiple sclerosis. Effective medical treatment can consist of repair or treatment of damaged functional parts by surgical or pharmacological techniques in an attempt to restore the natural sequence of micturition events. Complete restoration of function of course includes returning volitional control of the micturition reflex to the patient. Electronic stimulation techniques are known whereby muscular contractions can be induced in a manner mimicking the natural sequence of events. Thus, knowledge of normal micturition function, including neurological understanding of the lower urinary tract, coupled with an assessment of the damage incurred by the individual patient, facilitates medical treatment of and restoration of function to the neurologically disabled bladder. Diagnosis of a particular patient's micturition characteristics is greatly facilitated through the techniques of gas cystometry and sphincter electromyography.

Cystometry is a diagnostic procedure for evaluating bladder function whereby an accurate picture of normal and abnormal micturition physiology is derived. Cystometric evaluation of micturition disturbances permits an orderly system of classification of neurogenic bladders. The procedure involves distension of the bladder by filling it with a gas or liquid through an inserted catheter. As fluid is inserted interiorly of the bladder, the relation between intravesical bladder pressure and inputted volume of fluid is graphically determined. The principal observation made from the cystometrogram which results in the presence or absence of a detrusor reflex. Where a detrusor reflex is evoked by bladder filling, the patient may be asked to suppress the reflex as a test of detrusor volitional control. The patient's response will be graphically characterized by the cystometrogram (CMG). Cystometry may also be used to test the urodynamics of voiding. The latter technique provides for simultaneous measurement of urinary flow rate with intravesical pressures as voiding occurs concurrently with a detrusor reflex.

Sphinctor electromyography is a diagnostic technique in which micturition electrical responses of the urinary sphincters are graphically displayed. Electromyography has been used in detecting lesions of the lower motor neurons and peripheral nerves and in diagnosing primary skeletal muscle disease. The sphincter response is sensed by utilization of externally contacting electrodes. Usually, electronic amplifying apparatus is provided to process the sphincter signals sensed by the electrodes such that the signal may be displayed; for example, on a strip chart recorder. The electromyogram (EMG) produced by the technique provides a useful graphical monitor of sphincter electrical activity, particularly where a patient is unable to control voiding.

For example, the patient's ability to volitionally contract the sphincters (as is necessary to preserve continence) can be observed by the process to determine if supraspinal innervation is intact. Abnormal patterns of urinary sphincter action, which include detrusor sphinctor dyssynergia and uninhibited urinary sphincter relaxation can also be detected. Thus sphincter electromyography is a useful technique where a patient experiences difficulty with the urinary tract.

Sphincter electromyography is described in an article entitled "Neuro-Urological Selection of Patients for Restoration of the Micturition Reflex", which appears in the book *Neuralorganization and Its Relevance to Prosthetics*, edited by William S. Fields and published by Intercontinental Medical Book Corp., New York (1973); and in an article entitled "Sphincter Electromyography", appearing in Urologic Clinics of North America, Volume 1, No. 1, published February, 1974. Sphincter monitoring by mechanical devices is disclosed generally in U.S. Pat. No. 3,437,088, entitled "Apparatus for Measuring Esophageal Motility", issued to N. A. Crites on Nov. 25, 1969; and U.S. Pat. No. 2,541,520, entitled "Method and Apparatus to Indicate or Observe Progressive Exercise of Injured Sphincter Muscles", issued to A. H. Kegal on Feb. 13, 1951.

Combining electromyography with cystometry in the evaluation or neuromuscular dysfunction of the lower urinary tract has the potential of providing an understanding of pathophysiological relationships obscure to either technique used alone. For example, the combination of cystometry with concurrent sphincter electromyography facilitates analysis of the two essential elements of voiding, detrusor contraction and sphincter function. See, for example, an article entitled "Cystometric and Sphincter Abnormalities in Multiple Sclerosis", appearing in *Neurology*, Volume 23, No. 10 (1973). Experimental investigations have demonstrated that increasing bladder distention and detrusor reflex contraction produce attenuation of sphincter EMG activity. For effective voiding sphincter relaxation must occur, but for effective urinary continence reflexive external sphincter contraction must occur. The interaction which occurs during voiding provides for relaxation of the periurethral striated muscle component of the urinary sphincter concurrent with detrusor reflex contractions. With the foregoing background in mind, we have determined the desirability of producing concurrent recording of cystometrographic information and sphincter electromyographic information in order to facilitate diagnostic evaluation of micturition.

SUMMARY OF THE INVENTION

This invention relates generally to medical diagnostic apparatus. More particularly, the invention described herein relates to a method and apparatus for performing cystometry and sphincter electromyography.

In the preferred embodiment this invention comprises sphincter electromyography apparatus and fluid cystometry apparatus which are housed within a unitary enclosure, and which generate a combined graphical output from an integral, dual-trace strip chart recorder. The invention thus provides for convenient inspection and correlation of the bladder sphincter electrical activity and detrusor reflexes discussed earlier.

Both electromyography and cystometry are performed with a urinary catheter and at least one electromyographic electrode mounted on the catheter or on an anal plug. The catheter preferably includes a pair of electromyographic electrodes mounted in spaced apart relation on the bladder-engaging end thereof. The catheter is inserted through the urethra interiorly of the bladder, and is adapted to conduct a fluid, such as carbon dioxide, therethrough. The catheter is separately described and claimed herein.

The cystometry apparatus encompasses regulator apparatus for controllably delivering gas to the catheter, and electronic apparatus for continuously measuring the pressure of the gas inputted through the catheter to the bladder. Transducer means is provided for generating an electrical signal corresponding to catheter input pressure which is delivered for display to the strip chart recorder. A constant volume flow meter is provided to maintain a constant input into the catheter. Therefore, the cystometrogram which results accurately displays bladder pressure versus the volume of gas inputted thereto. The resulting trace adequately displays the detrusor reflex as well as other neurological events associated with bladder function. In the preferred embodiment the cystometry apparatus disclosed herein utilizes carbon dioxide gas inputted from a lecture bottle container. The lecture bottle is secured on a unique mounting system which enables empty containers to be quickly replaced.

The electromyographic apparatus is adapted to receive sphincter electrical signals from an electrode and to convert the signals into a form suitable for display over the strip chart recorder. Sphincter electrical signals may be derived, for example, from an hourglass-shaped anal plug, which must be inserted in the patient's anal opening. In the preferred embodiment, however, sphincter signals are derived from the aforementioned catheter electrodes. Such catheter electrodes preferably take the form of rings in circumferential engagement with the catheter.

In one form of the invention, sphincter electromyographic apparatus comprises electronic means for amplifying the sphincter electrical signals, comparator means for outputting a signal when the amplifier output exceeds a predetermined value, thereby providing noise protection, a monostable multivibrator for converting the comparator output to equal width pulses, a converter for generating another analog voltage in response to the equal width pulses, the analog voltage having an amplitude proportional to the frequency of the equal width pulses and unique oscillator means responsive to said analog voltage for generating an alternating current signal suitable to actuate the display recorder.

Thus an important advantage associated with this invention is that cystometric and electromyographic readings are simultaneously derived and simultaneously displayed. Moreover, preferably manually actuable event marker means is provided so that the patient can mark the onset of the urge to void, for example. Since the attendant physician can observe sphincter electrical activity at a given instant along with the corresponding detrusor reflex occurring at that time, important diagnostic benefits are realized.

Briefly summarized, the diagnostic method described herein comprises the steps of generating a cystometrogram, generating a sphincter electromyogram by sensing sphincter electrical activity through a catheter-mounted electrode, and simultaneously displaying the cystometrogram and the electromyogram; thereby correlating bladder neurological responses.

Thus a primary object of this invention is to provide apparatus for investigating and diagnosing urinary dysfunction.

Another object of this invention is to provide apparatus for performing gas cystometry.

A further object of this invention is to provide apparatus for performing sphincter electromyography.

Another important object of this invention is to provide apparatus whereby cystometry and sphincter electromyography may be simultaneously performed.

A related object of this invention is to provide diagnostic apparatus of the character described which will enable the attendant physician to correlate cystometry and electromyography signals derived from his patient. It is an important feature of this invention that the cystometrogram and the electromyographic trace generated at a particular instant in time may be readily compared for proper urological diagnosis.

Yet another object of this invention is to obviate the necessity of an anal plug or needle electrodes during sphincter electromyography. It is a feature of this invention that a unique catheter having an electromyographic electrode integrally mounted thereon may be employed rather than various prior art electrodes which are time-consuming and painful.

Still another important object of this invention is to provide cystometry apparatus in which bladder volume is linearized with respect to bladder pressure. Accordingly, fluid flow regulation means is provided to effectually correlate the time-base axis of the strip chart with correct bladder volume.

Another object of this invention is to provide unique diagnostic methods for investigating urological dysfunction.

These and other objects and advantages of our invention will become readily apparent as the following description is read in conjunction with the accompanying drawings wherein like reference numerals have been used to designate like elements throughout the several views:

BRIEF DESCRIPTION OF THE DRAWINGS

FIG. 1 is a perspective view of a micturition analyzer constructed in accordance with the teachings of this invention;

FIG. 2 is a partially fragmentary plan view of a unique catheter for use with cystometry and electromyography;

FIG. 3 is a partially fragmentary, pictorial view of a bladder showing the catheter properly positioned therein;

FIG. 4 is a block diagram of the cystometry apparatus described herein;

FIG. 5 is a block diagram of the electronic circuitry utilized by the electromyographic apparatus described herein;

FIG. 7 is a block diagram of the oscillator shown in FIG. 5;

DETAILED DESCRIPTION OF THE DRAWINGS

Figure 6:
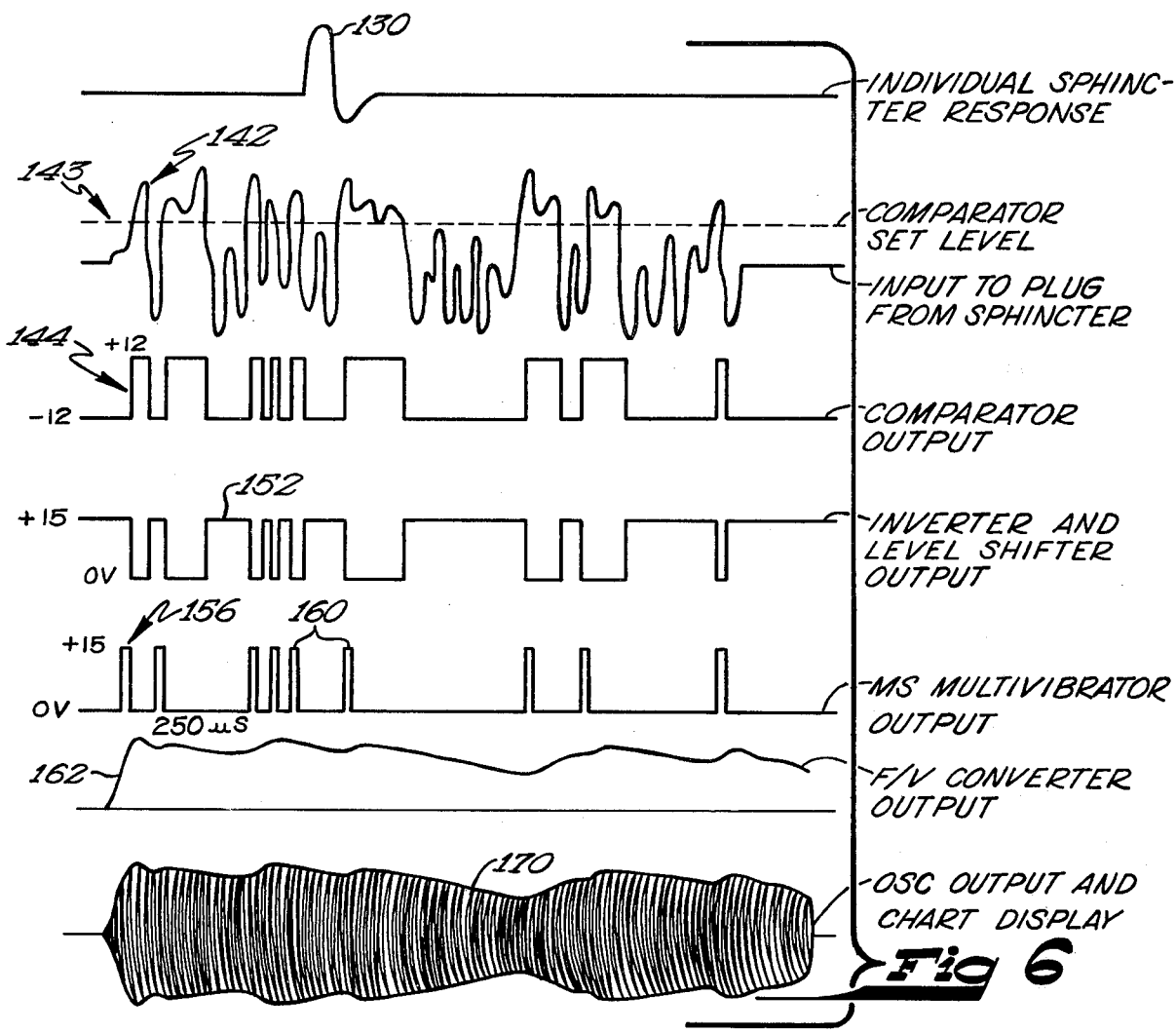
FIG. 6 shows a plurality of electrical waveforms associated with the apparatus of FIG. 5.

Referring now to the drawings and more particularly FIG. 1 thereof, electromechanical diagnostic apparatus for simultaneously (or independently) performing fluid cystometry and/or sphincter electromyography is designated generally by the reference numeral 10. Apparatus 10 comprises a generally cubical, box-like enclosure 12 which houses the apparatus and which has a front control panel 14 integral therewith on which a plurality of operating controls is mounted. A conventional strip chart recorder 16 is housed within enclosure 12 and mounted within an appropriate orifice in control panel 14. The strip chart recording apparatus continuously (in response to function switch 30) outputs a paper strip 18 on which information is continuously traced by conventional needles 20, 21 and 22. An electromyogram 24 is traced by needle 20 at the left side of the chart. The cystometrogram 26 is located at the right of the chart and traced by needle 22. A preferably hand held event marker 27 (which interconnects with the apparatus 10 at the back of the enclosure 12) may be manually actuated in order to mark preselected events on the strip chart. Thus, marker dots 28 and 29 are produced by needle 21 in response to actuation of push button event marker 27 and provide a convenient marking point on the strip chart for identifying significant events. The apparatus is energized by function switch 30, and a pilot light 32 is included to indicate that the apparatus is "on".

Cystometry is performed by catheterizing the patient and interconnecting the catheter via a preferably flexible tube (not shown) with gas output nozzle 34 at the front of the apparatus. The catheter will be described in more detail later in conjunction with FIGS. 2 and 3. Nozzle 34 is interconnected with a source of preferably carbon dioxide gas located interiorly of enclosure 12. To generate a cystometrogram, function switch 30 must be turned to its "record" position, whereupon strip chart 16 will be actuated and gas will be controllably outputted from nozzle 34 into the bladder of the patient. Gas flow rate is determined by adjustment of a flow meter control 36, and the output rate is displayed on flow meter 38. As the bladder fills with gas cystometrogram 26 will be generated and will record interior bladder pressure. The vertical axis (as viewed in FIGS. 8 thru 10) indicates bladder pressure, and the horizontal axis of the strip chart (again viewed as in FIGS. 8 thru 10) will indicate the corresponding volume of gas inputted to the bladder at that time. Importantly, the rate at which gas is delivered to the bladder is constant so that the time axis (the horizontal axis as viewed in FIGS. 8 thru 10) of the strip chart will linearly indicate the volume of gas inputted to the bladder at a given time. The cystometrogram will thus linearly relate bladder pressure to bladder volume.

Sphincter electromyography may be performed either concurrently with or independently of cystometry. The resultant electromyogram provides a graphical display and record of sphincter muscle electrical activity. Sphincter neural activity is monitored by appropriately placed electrodes which must be electrically interconnected with an input box 40 (through input jack 41 therein), which is connected to electromyography circuitry within enclosure 12 via a cable 42. Electromyography is initiated by turning function switch 30 into its "record" position, and by setting EMG sensitivity switch 44 to the lowest position necessary to obtain a good EMG tracing. Representative electromyographic (and cystometric) patterns will be discussed later in conjunction with FIGS. 8 thru 10.

Sphincter electrical signals are sensed by one or more contacting electrodes. Conventional needle electrodes will produce acceptable results when appropriately located in the sphincter. A conventional hourglass-shaped anal plug having at least one electrode integrally mounted thereon will produce acceptable results when inserted into the rectum of the patient to thereby monitor anal sphincter activity. Anal sphincter activity is known to generally correspond to urethral sphincter activity. However, the latter needle electrodes and anal plug do have certain limitations and difficulties associated with their use. The needle electrodes for example must be tediously inserted by a physician and they can be very painful to the patient. The anal plug is also painful and often awkward, and it is substantially ineffective where a flaccid anal sphincter is encountered.

Accordingly, urethral sphincter electrical activity is preferably monitored by at least one ring-shaped electrode mounted near the bladder-engaging end of a catheter (FIGS. 2 and 3). The use of catheter-mounted electrodes for electromyography is more efficient because, unlike prior art needle electrodes, a catheter may be inserted by a registered nurse rather than a doctor. Furthermore, catheter-mounted electrodes are less painful and irritating to the patient.

A flexible, preferably plastic catheter 50 which is ideally suited for use with the above-described apparatus is shown in FIGS. 2 and 3. Catheter 50 is comprised of a plurality of elongted, tubular lumen portions 52, 54 and 56, which are joined together to form an elongated shank portion 58. The main lumen 54 is adapted to input fluid, such as carbon dioxide or the like, through a discharge orifice 60 into the bladder for performing cystometry. Lumen 54 has an input end 62 which is adapted to be connected to a source of fluid such as gas nozzle 34 (FIG. 1). Lumen 52 interconnects with a balloon portion 66 near bladder-engaging end 64. After the catheter is inserted and properly positioned, balloon portion 66 is inflated by connecting end 68 of lumen 52 to an appropriate gas souce. As illustrated in FIG. 3, inflation of balloon 66 will prevent inadvertent withdrawal of the catheter 50 from the bladder.

Ring-shaped electrodes 70 and 72 are mounted in spaced apart relationship on catheter 50 near balloon portion 66 near the bladder-engaging end of the catheter. The electrodes 70 and 72 are preferably positioned such that they will contact the external urethral sphincter muscle when catheter 50 is appropriately positioned within the bladder, thereby sensing urethral sphincter electrical responses. Electrodes 70 and 72 are respectively interconnected with the electromyographic apparatus through a pair of conductors 74 and 76. Alternatively, it is contemplated that sphincter neural impulses sensed by electrodes 70 and 72 could be transmitted to the electromyographic apparatus through conventional telemetry apparatus. Conductors 74 and 76 are preferably housed within lumen 56 which prevents the conductors from contacting urine or gas. It is apparent that conductors 74 and 76 could alternatively be positioned, for example, in lumen portion 54. In the preferred embodiment conductors 74 and 76 will be electrically connected to input box 40 (FIG. 1) so that sphincter electromyography can proceed. Thus, with the use of catheter 50 sphincter electromyography and gas cystometry may be simultaneously performed. Of course, the catheter will function adequately during either procedure alone. After the completion of the tests balloon portion 66 is deflated and the catheter is withdrawn from the bladder.

The cystometry portion of the apparatus is shown in FIG. 4. In the preferred embodiment cystometry is performed with carbon dioxide, rather than with air, physiologically inert liquids, or other fluids. Carbon dioxide is supplied from a small lecture bottle size tank 80 and delivered to a regulator 82 via a manifold 84. Regulator 82 reduces the high manifold pressure from approximately 900 psi to approximately 15 psi. The low pressure output of regulator 82 is delivered past a relief valve 86 and to a differential regulator 88 through a manifold 90. Safety relief valve 86 opens at a predetermined pressure in case of misfunction of regulator 82. Regulator 88 provides a constant low differential pressure between its outlet line 91 and its reference line 98. Gas flows along a line 91 to a solenoid valve 92 and a needle valve 94, which is connected to flow meter 38 via line 95. Solenoid valve 92 is opened when function switch 30 is turned to record, permitting gas to flow. Needle valve 94 can be adjusted by the operator to vary the cystometry gas output rate by manipulating knob 36 (FIG. 1). Flow meter 38 outputs fluid to a junction 96, to which regulator 88 is also concerned via a return line 98. The constant pressure across the needle valve 94 provided by differential regulator 88 provides a constant flow independent of outlet pressure at junction 96. The pressure appearing in junction 96 is limited by a relief valve 100 which opens at a predetermined pressure to provide a mechanical safety feature. Gas nozzle 34 receives gas through junction 96 and delivers it to the catheter 50 during cystometry.

A pressure transducer 102, which is interconnected to junction 96 via a line 104, outputs an electrical signal which is proportional to catheter input pressure. In the preferred embodiment, the pressure transducer output varies from approximately 2.5 to 12.5 volts for a pressure variation between 0 and 15 psi. The transducer voltage is inputted to an amplifier 105 via a line 106 and converted to a control voltage which appears along a line 108 and is suitable for driving the strip chart recorder.

The pressure-responsive output of amplifier 105 also reaches a comparator 110 through lines 108 and 112. Comparator 110 is adjusted to respond when the input voltage on line 112 reaches a predetermined level. In the preferred embodiment comparator 110 is responsive to a catheter input pressure of approximately 150 centimeters of water. When comparator 110 is actuated solenoid valve control 114 will be actuated via line 115. When control 114 is triggered (by function switch 30, for example) solenoid valve 92 will close, thereby cutting off the flow of gas through flow meter 38 to catheter 50. Solenoid valve 92 remains open as long as an appropriate control voltage from control 114 appears on line 116. When control 114 is triggered by comparator 110, or when a power failure occurs, for example, line 116 will go low and solenoid valve 92 will immediately close, thereby providing failsafe operation.

The strip chart recorder is a conventional dual-trace strip chart manufactured by the M.F.E. Corporation. The paper strip chart is outputted linearly with respect to time. Flow meter 38 provides a constant gas flow rate to catheter 50, so that the volume of fluid inputted to the bladder is a linear function with respect to time. Thus, the resulting cystometrogram may be readily inspected to determine the volume of gas inputted to the bladder at a given instant in time.

The electromyographic electronic circuitry 120 is shown in block form in FIG. 5. Sphincter electrical responses from appropriate electrodes are delivered via input lines 122 and 124 to a dual input amplifier 126 which provides an output on line 128. In FIG. 6 an individual sphincter nerve cell response is illustrated by a trace 130, and the trace resulting from a plurality of sphincter signals is identified as waveform 142. The signal on line 128 is filtered and amplified by the combination of band pass filter 131, amplifier 132, band pass filter 134, variable gain amplifier 136, and band pass filter 138, which delivers an output to a comparator 140 via a line 139. The electromyography sensitivity control 44, discussed earlier in conjunction with FIG. 1, varies the gain of amplifier 136.

Comparator 140 receives processed sphincter electrical signals identified by trace 142 in FIG. 6. Comparator 140 generates an output 144 whenever its input voltage reaches a predetermined level, identified generally by dotted line 143. The variable width pulses 144 outputted by the comparator are processed by an inverter and level shifter 150, which delivers a waveform 152 to a monostable multivibrator 154. The monostable output 156 consists of a series of equal width pulses which are delivered to a frequency-to-voltage converter 158. Converter 158 produces an analog voltage output 162 having a voltage proportional to input frequency. The output of converter 158 is buffered by inverting amplifier 164 and delivered to an oscillator 166 via a line 167. Oscillator 166 outputs a low frequency alternating current signal 170 which is in effect envelope modulated by signal 162. Signal 170 is received by the strip chart recorder for generation of an electromyogram therefrom.

Oscillator 166 (FIG. 7) outputs a low frequency triangular waveform whose peak-to-peak voltage is proportional to the output of frequency-to-voltage converter 158 (FIG. 5). Initially the voltage appearing across capacitor 171 is zero volts, and at this time the output of comparator 172 appearing on line 174 turns on diode switches 176 and 178. Waveform 162 (FIG. 6) which is outputted by converter 158 is transmitted to the input of switches 176 and 178 via lines 167, 168 and 169. Actuation of diode switch 178 causes waveform 162 to be delivered via line 180 to a plus input of comparator 172. Actuation of switch 176 causes waveform 162 to be inverted in amplifier 184 and delivered to a current source 186 via a line 187. Source 186 then charges capacitor 171 positively through line 188. The voltage across capacitor 171 reaches comparator 172 along a line 190, and when this voltage equals the voltage simultaneously appearing along line 180, the output of comparator 172 will turn off switches 176 and 178 by going negative. Simultaneously the negative output of comparator 172 turns on diode switches 192 and 194 via a line 196. Switch 194 receives a signal corresponding to inverted waveform 162 from an inverter 198 via a line 200 and delivers this signal via line 202 to an input of comparator 172. Diode switch 192, which has also been actuated by the signal appearing on line 196, transmits inverted waveform 162 to an inverting amplifier 204 which delivers a signal similar to waveform 162 to another current source 206 which negatively charges capacitor 171 via a line 208 until the voltage along line 190 at the right input to comparator 172 equals the voltage along line 202. When this occurs comparator 172 will output a positive voltage on lines 174 and 196 turning on switches 176 and 178 and turning off switches 192 and 194. Capacitor 171 will then charge positively in the manner previously described and the cycle will be repeated.

The oscillating voltage appearing across capacitor 171 is buffered by an isolation amplifier 210 which provides the output 170 for the strip chart recorder. The oscillation frequency, which in the preferred embodiment is approximately 5 Hz., is controlled by the value of capacitor 171. The operating frequency is made independent of the voltage appearing on line 167 by making the magnitude of the current outputted by current sources 206 and 186 proportional to the voltages inputted thereto. It will be obvious to those skilled in the art that a variety of conventional oscillator circuits may be substituted for the preferred oscillator circuitry just described.

Figure 8:
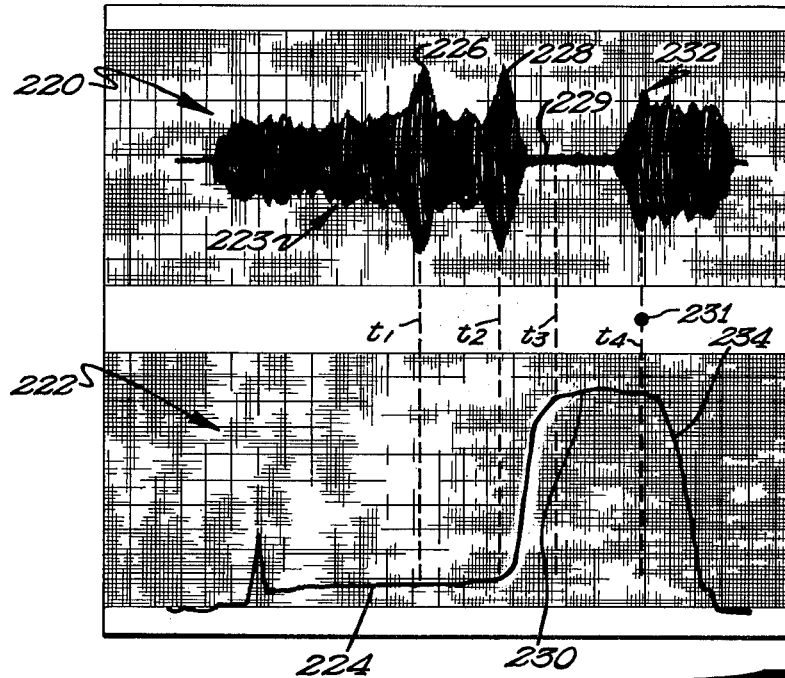
FIG. 8 is a combined sphincter electromyogram and cystometrogram outputted by the apparatus of FIG. 1, and illustrating the patterns obtained from a healthy volunteer.
Figure 9:
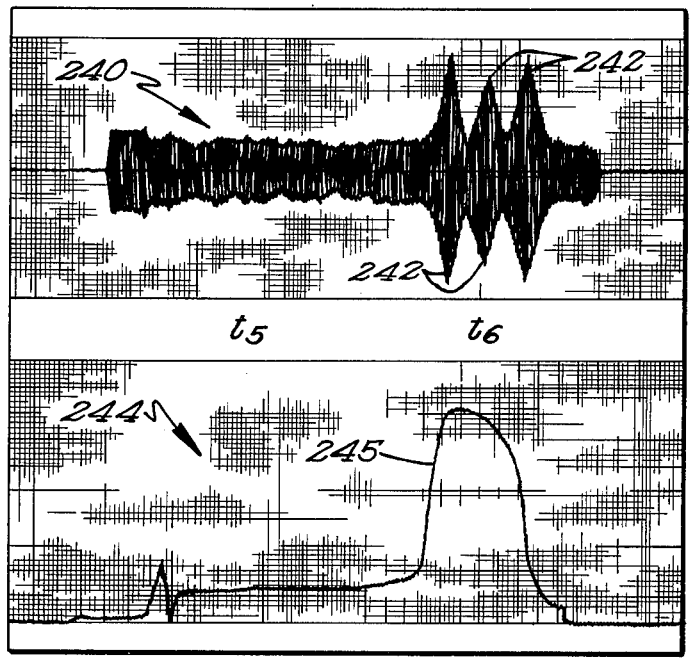
FIG. 9 is a strip chart recording similar to FIG. 8 but illustrating detrusor sphincter dyssynergia.
Figure 10:
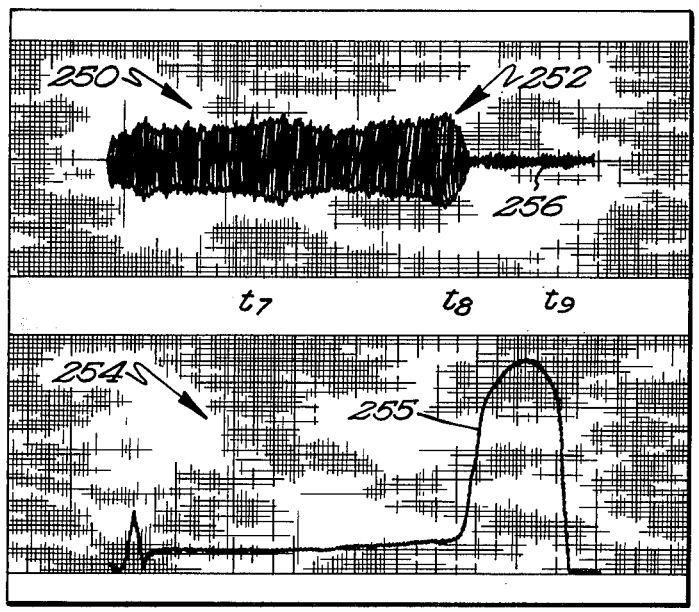
FIG. 10 is a strip chart recording similar to FIGS. 8 and 9 but illustrating uninhibited sphincter relaxation.

Referring now to FIGS. 8 thru 10, the upper trace outputted by the strip chart recorder comprises an electromyogram (EMG) and the lower trace comprises a cystometrogram (CMG). The vertical scale in the electromyogram corresponds generally to the amplitude of sphincter electrical activity. The horizontal axis of each electromyogram corresponds to time. During generation of an electromyogram sensitivity control 44 (FIG. 1) should be adjusted by the operator to produce the desired EMG trace amplitude.

The vertical axis in each cystometrogram represents bladder pressure. The horizontal axis represents the volume of gas inputted to the bladder. Because the cystometry gas flow rate is constant, each horizontal division represents an equal increase in bladder volume. Thus the linearizing technique employed by the apparatus facilitates quantitative systemetric bladder evaluation. The volume of gas represented by each horizontal increment is of course a linear function of the gas flow rate observable on flow meter 38 (FIGS. 1 and 4).

Electromyogram 220 and cystometrogram 222 (FIG. 8) represent normal patterns obtained from a healthy volunteer. At the start of the test sphincter electrical activity is indicated generally by EMG portion 223 while the bladder is gradually being filled with gas, as indicated by CMG portion 224. At time $t1$ the EMG has an increased activity portion 226 which indicates the first sensation of bladder fullness. At time $t2$ EMG portion 228 indicates a burst of sphincter electrical activity coinciding with a feeling of urgency. At time $t3$ EMG portion 229 indicates sphincter relaxation, and CMG portion 230 indicates a simultaneous intravesical pressure increase due to detrusor contraction. The latter events are indicative of the normal micturition reflex.

At time of $t4$ the examinee has volitionally suppressed the detrusor reflex, tightening the sphincter muscles to close off the urethra. At this time marker dot 231 has been recorded by actuation of event marker 27 (FIG. 1). Increased sphincter electrical activity is indicated generally by EMG portion 232. Approximately 10 seconds later detrusor muscles relax, resulting in the decreased bladder pressure indicated by CMG segment 234.

The strip chart recordings shown in FIG. 9 indicate detrusor sphincter dyssynergia. At time $t5$ the patient has been requested to contract a sphincter muscle, and electromyogram 240 illustrates the failure of the sphincter muscles to contract at this time. By way of comparison, electromyogram 220 (FIG. 8) shows increased sphincter electrical activity in response to volitional contraction at time $t4$. The minimal sphincter activity at time $t5$ is immediately apparent from visual inspection of EMG 240. At time $t6$ increased sphincter activity is indicated by EMG portion 242 while CMG 244 has a portion 245 indicating simultaneously increasing bladder pressure. This differs from the normal micturition reflex shown in FIG. 8 in that rising bladder pressure (segment 245) occurs concurrently with increased sphincter electrical activity (as indicated by EMG segment 242).

Uninhibited sphincter relaxation is indicated by the patterns shown in FIG. 10. Electromyogram 250 indicates that the patient is unable to voluntarily contract the sphincter muscle at time $t7$. The detrusor reflex occurs at time $t8$, whereupon the sphincter relaxes (as indicated by EMG segment 252). Simultaneously, cystometrogram 254 (and more particularly segment 255 thereof) indicates rising intravesical pressure. Sphincter relaxation is indicated by EMG segment 256. By time $t9$, however, the patient is unable to maintain urinary continence because of failure to contract the sphincter muscle (as indicated by the lack of increased EMG activity at this time).

We anticipate that various changes and modifications may be made in the size, shape, and structural arrangement of the invention disclosed herein without departing from the spirit and scope of our invention as defined by the following claims.

What is claimed is:

1. Electromechanical apparatus for diagnosing urinary bladder dysfunction comprising:
    cystometry means for determing the presence or absence of a bladder detrusor reflex, said cystometry means comprising:
        an elongated urinary catheter comprising a tubular, lumen portion having an input end and a bladder engaging output end with a discharge orifice therein for introducing pressurizing fluid into a patient's bladder;
        fluid output supply means attached to said input end of said catheter; and
        electronic means connected to said catheter and operative to generate a first electrical signal corresponding to interior bladder fluid pressure;
    electromyography means for monitoring urethral sphincter electrical activity, said electromyography means comprising:
        a pair of electrodes capable of sensing urethral sphincter electrical activity longitudinally spaced apart on the external surface of said catheter near said bladder engaging end thereof; and
        electromyographic circuit means interconnected with said pair of electrodes for generating a second electrical signal corresponding to said urethal sphincter electrical activity; and
    instrument means for simultaneously displaying said first electrical signal and said second electrical signal.

2. The combination as defined in claim 1 wherein said instrument means comprises strip chart recorder means for recording a first trace in response to said first electrical signal and a second trace in response to said second electrical signal.

3. The combination as defined in claim 2 wherein said apparatus comprises manually actuable marker means associated with said strip chart recorder means for identifying selected events.

4. The combination as defined in claim 1 wherein said cystometry electronic means for generating said first electrical signal comprises:
   pressure transducer means interconnected with said fluid output supply means for generating a third electrical signal proportional to fluid output pressure; and
   means for amplifying said third electrical signal thereby outputting said first electrical signal.

5. The combination as defined in claim 1 wherein:
   said pair of electrodes are positioned at spaced apart locations on said urinary catheter such that they will contact the external urethral sphincter of a patient when said catheter is properly inserted within the urethra of a patient in position to inject pressurizing fluid into the patient's bladder through said lumen portion.

6. The combination as defined in claim 1 wherein a positive shutoff valve is positioned between said fluid output supply means and said input end of said lumen portion of said catheter; and
   control means operative to open and close said shutoff valve;
   comparator means operatively associated with said control means and responsive to said first electrical signal to operate said control means to close said valve when the amplitude of said first electrical signal reaches a predetermined valve.

7. The combination as defined in claim 6 including a function control switch on said instrument means connected to said control means for said valve and operative to open and close said valve to initiate and stop operation of said cystometry means.

8. The combination as defined in claim 1, and further including:
   a source of fluid;
   differential pressure regulator means for regulating fluid pressure, said differential regulator means comprising a fluid input in fluid flow communication with said source of fluid, an output, and a pressure reference line in fluid flow communication with said fluid output supply means;
   selectively variable flow meter means having an input in fluid flow communication with said differential pressure regulator means output and an output in fluid flow communication with said fluid output supply means for effecting a user programmable constant volume output rate of fluid from said fluid output supply means, thereby linearizing the volume of fluid outputted by said apparatus with respect to time; and wherein
   said instrument means comprises strip chart recorder means for recording a first trace in response to said first electrical signal and a second trace in response to said second electrical signal, said first trace reflecting said interior bladder pressure on a vertical axis and said linear constant fluid volume on a horizontal axis.

9. The combination as defined in claim 8 wherein said electromyographic circuit means comprises:
   means for amplifying said sphincter electrical signals, said amplifying means having an output;
   comparator means for generating a first pulse signal when said amplifier means output exceeds a predetermined value;
   monostable means for generating equal width pulses in response to said first pulse signals;
   converter means for generating an analog voltage in response to said equal width pulses, said analog voltage having an amplitude proportional to the frequency of said equal width pulses; and
   means responsive to said analog voltage for outputting said second electrical signal.

10. The combination as defined in claim 9 wherein said means for outputting said second electrical signal comprises oscillator means for generating an alternating current signal having an amplitude proportional to said analog voltage.

11. The combination as defined in claim 1 wherein:
    said urinary catheter includes a second, tubular lumen portion; and
    conductor means attached to said pair of electrodes in said electromyographic circuit means for transmitting electrical signals sensed by said electrodes to said instrument means, said conductor means being contained within said second lumen portion to prevent contamination thereof.

12. The combination as defined in claim 1 wherein:
    said pair of spaced electrodes are ring shaped and extend circumferentially around said bladder engaging end of said catheter.

13. Diagnostic cystometry apparatus comprising:
    a source of fluid;
    an elongated urinary catheter adapted to be inserted interiorly of a patient's bladder through the urethra, said catheter having at least one fluid conducting lumen passage therein for delivering fluid to the bladder;
    fluid output supply means connected to said source of fluid and attached to said catheter lumen passage for insufflating a bladder;
    transducer means for generating an electrical signal proportioned to interior bladder fluid pressure;
    recording means for displaying said electrical signal;
    a positive shutoff valve between said fluid output supply means and said catheter lumen passage;
    control means operative to open and close said shutoff valve; and
    comparator means operatively associated with said control means and responsive to said electrical signal to operate said control means to close said valve when the amplitude of said electrical signal reaches a predetermined value.

14. Cystometry apparatus as defined in claim 13 wherein a function switch is connected to said control means for said valve and is operative between different positions to open and close said valve to initiate and stop operation of said cystometry apparatus.

15. A method for diagnosing micturition and urinary bladder dysfunction comprising the steps of:
    inserting a catheter having at least one fluid lumen therein interiorly of a patient's bladder through the urethra, said catheter having at least one electrode on the external surface thereof positioned to contact the urethral sphincter of the patient when said catheter is inserted in the urethra;
    directing fluid under pressure through said catheter lumen into the patient's bladder;
    monitoring fluid pressure at said catheter, and generating a first electrical signal in response to same;

directly sensing urethral sphincter electrical responses to said fluid pressure with said electrode on said catheter simultaneously with the monitoring of said fluid pressure;

generating a second electrical signal corresponding to said urethral sphincter electrical responses; and simultaneously displaying said first and second electrical signals on a single recording instrument to thereby directly correlate bladder and urethral sphincter responses to predetermined bladder pressures generated by said fluid under pressure.

16. The method as defined in claim 15 wherein said method further comprises the steps of:

supplying said fluid to said catheter at a constant volume input rate through a fluid flow regulator, thereby inputting fluid through said catheter into the bladder to insufflate same; and linearizing recorded bladder volume by regulating the differential pressure between an input and an output of the fluid flow regulator.

17. The method as defined in claim 15 wherein:

said displaying step for said second electrical signal comprises the steps of:

amplifying said sphincter electrical responses thereby generating an amplified signal;

generating a first pulse signal when said amplified signal exceeds a predetermined value;

generating equal width pulses in response to said first pulse signal;

generating an analog voltage in response to said equal width pulses, said analog voltage having an amplitude proportional to the frequency of said equal width pulses; and generating an alternating current signal having an amplitude proportional to said analog voltage and actuating a recording with said alternating current signal to thereby display said second electrical signal.

* * * * *